US010531072B2

(12) United States Patent
Popilka et al.

(10) Patent No.: US 10,531,072 B2
(45) Date of Patent: Jan. 7, 2020

(54) CALIBRATION DEVICE AND METHOD FOR CALIBRATING A DENTAL CAMERA

(71) Applicant: DENTSPLY SIRONA, Inc., York, PA (US)

(72) Inventors: Bjorn Popilka, Hemsbach (DE); Frank Thiel, Ober-Ramstadt (DE); Frank Forster, Munich (DE)

(73) Assignee: DENTSPLY SIRONA INC., York, PA (US)

( * ) Notice: Subject to any disclaimer, the term of this patent is extended or adjusted under 35 U.S.C. 154(b) by 432 days.

(21) Appl. No.: 14/440,478

(22) PCT Filed: Nov. 4, 2013

(86) PCT No.: PCT/EP2013/072884
§ 371 (c)(1),
(2) Date: May 4, 2015

(87) PCT Pub. No.: WO2014/068097
PCT Pub. Date: May 8, 2014

(65) Prior Publication Data
US 2015/0288952 A1    Oct. 8, 2015

(30) Foreign Application Priority Data

Nov. 2, 2012 (DE) .................. 10 2012 220 048

(51) Int. Cl.
| H04N 13/246 | (2018.01) |
| A61B 5/107 | (2006.01) |
| G01B 11/25 | (2006.01) |
| G01B 21/04 | (2006.01) |
| A61B 5/00 | (2006.01) |

(Continued)

(52) U.S. Cl.
CPC ......... *H04N 13/246* (2018.05); *A61B 5/1077* (2013.01); *A61B 5/1079* (2013.01);
(Continued)

(58) Field of Classification Search
CPC ..... G01B 11/25; G01B 11/24; G01B 11/2513; G01B 11/002; G01B 11/2518;
(Continued)

(56) References Cited

U.S. PATENT DOCUMENTS

| 5,760,925 A | 6/1998 | Saund et al. |
| 5,991,437 A | 11/1999 | Migdal et al. |

(Continued)

FOREIGN PATENT DOCUMENTS

| DE | 4011780 C1 | 9/1991 |
| DE | 19536297 A1 | 4/1997 |

(Continued)

OTHER PUBLICATIONS

German Office Action dated Dec. 17, 2012, in German Patent Application No. 10 2012 220 048.7.

(Continued)

*Primary Examiner* — Farhan Mahmud
(74) *Attorney, Agent, or Firm* — Dentsply Sirona Inc.

(57) ABSTRACT

The invention relates to a method and a calibration device for calibrating a dental camera (1), which is based on a fringe projection method for optically measuring a dental object (10) in three dimensions, comprising a projection grid (2) for generating a projection pattern (3) that consists of a plurality of fringes (5), and an optical system (4) that projects the generated projection pattern (3) onto the object (10) to be measured. In a first step, a reference surface (74) with known dimensions is measured by the dental camera (1) using the fringe projection method. Actual coordinates (33, 36) of a plurality of measurement points (11) are determined on the reference surface (74), and the determined actual coordinates (33, 36) are compared to target coordinates (34) of the measurement points (11) on the reference surface (74). In the following method step, proceeding from (Continued)

the deviations (35, 37) between the actual coordinates (33, 36) and the target coordinates (34), a plurality of compensation values (40, 50, 51, 52, 53) are calculated for the individual fringes (5) of the projection pattern (3).

11 Claims, 3 Drawing Sheets (51) Int. Cl.
G06T 7/80 (2017.01)
G06T 7/521 (2017.01)
H04N 17/00 (2006.01)
A61C 9/00 (2006.01)

(52) U.S. Cl.
CPC ........ *A61B 5/4547* (2013.01); *G01B 11/2513* (2013.01); *G01B 21/042* (2013.01); *G06T 7/521* (2017.01); *G06T 7/80* (2017.01); *H04N 17/002* (2013.01); *A61C 9/0053* (2013.01); *G06T 2207/10028* (2013.01); *G06T 2207/30208* (2013.01)

(58) Field of Classification Search
CPC ....... G01B 9/02057; G03F 7/706; G06T 7/80; A61C 13/0004; A61C 9/0053; G01S 17/89
See application file for complete search history.

(56) References Cited

U.S. PATENT DOCUMENTS

| | | | |
|---|---|---|---|
| 6,940,664 | B1 | 9/2005 | Pilu |
| 7,596,287 | B2 | 9/2009 | Wolf et al. |
| 2002/0006217 | A1 | 1/2002 | Rubbert et al. |
| 2002/0163651 | A1* | 11/2002 | Imaizumi ............. G01B 11/306 356/605 |
| 2005/0046873 | A1* | 3/2005 | Suzuki ............... G01B 11/2527 356/605 |
| 2005/0099638 | A1 | 5/2005 | Quadling et al. |
| 2007/0046663 | A1 | 3/2007 | Brinkmann et al. |
| 2007/0085849 | A1* | 4/2007 | Kosolapov ......... G01B 11/2509 345/419 |
| 2008/0062434 | A1 | 3/2008 | Diefenbacher |
| 2008/0259411 | A1 | 10/2008 | Karlsson |
| 2009/0046301 | A1 | 2/2009 | Asakura et al. |
| 2012/0092461 | A1 | 4/2012 | Fisker et al. |

FOREIGN PATENT DOCUMENTS

| | | |
|---|---|---|
| DE | 10133568 A1 | 1/2003 |
| DE | 10 2004 052 199 A1 | 4/2006 |
| DE | 600 27 529 T2 | 9/2006 |
| EP | 1650529 A1 | 4/2006 |
| EP | 1757902 A1 | 2/2007 |
| WO | 2006/036110 A1 | 4/2006 |
| WO | 2012/048889 A1 | 4/2012 |

OTHER PUBLICATIONS

German Office Action dated Mar. 12, 2012, in German Patent Application No. 10 2012 220 048.7.
International Preliminary Report on Patentability in PCT Application No. PCT/EP2013/072884, dated May 12, 2014.
English Translation of International Search Report in PCT/EP2013/072884, dated Feb. 17, 2014.

* cited by examiner

CALIBRATION DEVICE AND METHOD FOR CALIBRATING A DENTAL CAMERA

AREA OF TECHNOLOGY

The invention relates to a method and a calibration device for calibrating a dental camera which is based on a fringe projection method for optically measuring a dental object in three dimensions, comprising a projection grid for generating a projection pattern that consists of a plurality of fringes, and an optical system that projects the generated projection pattern onto the object to be measured.

PRIOR ART

A number of fringe projection methods are known from the prior art for optically measuring in three dimensions. In these methods, a projection pattern is projected onto the object to be measured. Subsequently, using a triangulation method, 3-D coordinates of the measurement points on the object are calculated on the basis of the distorted projection pattern. From a cloud of measurement points, a 3-D model of the object is then calculated.

A disadvantage of this method is that production errors in the projection grid, or optical errors of the optical system, can cause the generated 3-D model to possess measuring errors in comparison to the actual dimensions of the object. The production errors of the projection grid can for example lead to an erroneous fringe width, or to incorrect distances between the fringes. Optical errors in the optical system can for example be distortions that distort the projection pattern.

The object of the present invention is therefore to provide a method for calibrating a dental camera to compensate for measuring errors caused by the production errors or optical imaging errors.

DESCRIPTION OF THE INVENTION

The invention relates to a method for calibrating a dental camera which is based on a fringe projection method for optically measuring a dental object in three dimensions. The dental camera comprises a projection grid for generating a projection pattern that consists of a plurality of fringes, and an optical system that projects the generated projection pattern onto the object to be measured. In a first step of the method, a reference surface with known dimensions is measured by the dental camera using the fringe projection method. Actual coordinates of a plurality of measurement points are determined on the reference surface. Then, the determined actual coordinates are compared to known target coordinates (desired coordinates) of the measurement points on the reference surface with known dimensions. In the following method step, proceeding from the deviations between the actual coordinates and the target coordinates, a plurality of compensation values are calculated for the individual fringes of the projection pattern. These calculated compensation values are then taken into account when measuring the dental object in order to compensate for the deviations between the actual coordinates and target coordinates.

The reference surface is a calibration plate which is provided with a plurality of markings, and the markings are used to determine the precise position and alignment of the calibration plate relative to the dental camera. Then the deviations between the actual coordinates and calibration plate are determined along a direction perpendicular to the calibration plate.

The result of the calibration is a matrix consisting of compensation values which are used in a compensation method step while measuring the object on the projection pattern consisting of parallel fringes to correct the projection pattern, and then by using the fringe projection method, a three-dimensional image of the object is calculated on the basis of the corrected projection pattern.

In a fringe projection method, a pattern consisting of a plurality of parallel fringes is projected onto the object to be measured and, using a triangulation method, a three-dimensional image of the object is generated which is based on the distortion of the fringes.

It is possible, e.g., to color-code the fringes to enable identification. For this, a pattern consisting of a plurality of colored fringes is projected onto the object. Then the depth coordinates for the measurement points are determined, and a 3D model of the object is generated. The colored fringes can be clearly identified by their color. For example, four colored fringes and/or three color transitions can be used for color-coding the colored fringes. The colored fringes can for example be generated using a slide.

The fringe width of such fringe projection methods can for example be 150 μm in the measured volume of the object to be measured.

For the optical measurement, a different fringe projection method can also be used in which the fringes are coded using different optical properties such as intensity, color, polarization, coherence, phase, contrast, location or propagation time.

The projection grid to generate the projection pattern can for example be a slide through which light is passed and by means of which the parallel fringes are generated. The reference surface can for example be a flat or any three-dimensional surface such as a hemisphere. A production error of the projection grid or an imaging error of the optical system causes deviations between the actual coordinates and target coordinates of the measurement points on the reference surface. To compensate, compensation values are calculated for the individual fringes. These compensation values can be saved in a memory and used later on the projection pattern during measurement after calibration before calculating the three-dimensional image using the corrected projection pattern. This compensates for deviations between the actual coordinates and the target coordinates.

The markings can for example be rectangular markings which are arranged at fixed distances relative to each other. This allows the distance as well as the alignment of the reference surface relative to the camera to be calculated by a computer using the distances between the markings. No fitting by using the actual coordinates of the measurement points is required, since the position is already determined using the markings. Deviations between the actual coordinates and the calibration plate can hence be calculated directly, using a computer.

To determine the position of the reference surface, the known calibration method of Tsai which appears in the literature ("A Versatile Camera Calibration Technique for High-Accuracy 3D Vision Metrology Using Off-the-Shelf Cameras and Lenses", 1987) or the known method of Zhang ("A flexible new technique for camera calibration", 2000), which also appears in the literature, can be used.

An advantage of this method is that the deviations which arise due to production errors or imaging errors by the optical system are compensated, and the image quality is thereby improved.

The compensation values of such a matrix can for example be displacement vectors which represent a necessary displacement of the respective parallel fringes in order to compensate for the deviations between the actual coordinates and the target coordinates for the respective fringes. When calculating a three-dimensional image, the matrix consisting of compensation values is first used on the projection pattern, and only afterward are the 3-D coordinates of the measurement points on the object calculated using the corrected projection pattern.

Advantageously, the reference surface can be a plane, and the deviations between the actual coordinates and the target coordinates can be determined by fitting a reference plane using the actual coordinates by means of the least squares method, and then the deviations between the actual coordinates and the reference plane can be determined along a direction perpendicular to the reference plane.

The precise position of the reference surface relative to the dental camera is hence determined by the fitting. With a flawless projection grid and flawless optical system, all target coordinates would hence lie in the plane of the reference surface such that the actual coordinates would correspond with the target coordinates.

Advantageously, the deviations between the actual coordinates and the target coordinates can be determined from a number of images for different distances and alignments of the reference surface relative to the dental camera.

The distortions caused by an optical error can be depth-dependent such that the deviations between the actual coordinates and the target coordinates can change depending on the distance of the reference surface relative to the dental camera. By determining the compensation values for different distances, the depth-dependent optical image errors can also be compensated.

Advantageously, the images can be taken using a calibration device which has a first holding device for the dental camera and a second holding device for the reference surface which can be adjusted in a specific manner in a plurality of steps relative to the first holding device.

Such a calibration device makes it possible to change the distance and alignment of the camera in steps relative to the reference surface. Images can hence be taken for different distances and angles between the reference surface and dental camera, and then compensation values can be determined for the individual fringes for each of the images. The first holding device and second holding device can for example be connected by means of a threaded joint.

Advantageously, for each edge of a fringe, only one compensation value may be calculated, for the purpose of indicating a necessary displacement of this edge in the plane of the projection grid to compensate for the deviations of this edge.

In the fringe projection method, the two edges of each fringe are evaluated to calculate the 3-D coordinates of the measurement points along these edges. The compensation value for an edge can for example be calculated by determining deviations between the actual coordinates and the target coordinates for all measurement points of the respective edge, and then forming (calculating) an average of these deviations. The corresponding compensation value is then calculated using this average value of the deviations.

Advantageously, each edge of a fringe can be divided into a plurality of sectors, wherein a compensation value is calculated for each sector which indicates a necessary displacement of this sector in the plane of the projection grid to compensate for the deviations for this sector.

Each edge is thus divided into a plurality of sectors to improve the compensation. If an edge is wavy, it is not enough to displace the entire edge. Instead, an independent compensation value is calculated for each of the sectors in order to compensate for the errors for that respective sector.

Advantageously, the deviations between the actual coordinates and the target coordinates can be determined by taking a plurality of three-dimensional images of the reference surface in the same position and alignment relative to the dental camera, with the deviations from the individual images being averaged in order to reduce non-systematic errors generated by noise signals.

Errors caused by noise signals are thereby averaged out so that only the systematic error remains which, for example, is caused by a production error of the projection grid, or by imaging errors of the optical system.

An additional object of the invention is a calibration device for calibrating a dental camera which is based on a fringe projection method for optically measuring a dental object in three dimensions, wherein the dental camera comprises a projection grid for generating a projection pattern that consists of a plurality of fringes, and an optical system that projects the generated projection pattern onto the object to be measured. The calibration device has a first holding device for the dental camera and a second holding device for a reference surface, wherein the first holding device can be adjusted relative to the second holding device such that a number of defined distances and/or alignments can be brought about between the dental camera and the reference surface.

The above-described method can hence be used to perform the calibration of the dental camera. By means of this calibration device, a number of images can be taken for different distances and/or alignments between the dental camera and the reference surface. Then a matrix consisting of compensation values can be calculated for each of the images and used to correct the projection pattern. Distance-dependent imaging errors caused by a faulty optical system can be compensated in this manner.

Advantageously, the first holding device can have an inner thread, and the second holding device can have an outer thread which engages in the inner thread of the first holding device. By rotating the first holding device relative to the second holding device, the distance and alignment of the dental camera relative to the reference surface can hence be changed in defined steps.

By means of such a threaded connection, the distance and alignment of the reference surface relative to the camera can be easily changed stepwise by rotation.

Advantageously, the flat reference surface can be arranged in the second holding device at an angle between 50° and 70° relative to a middle axis of the outer thread. The angle can in particular be 65°.

By means of the rotation, the height is adjusted in the direction of the middle axis of the outer thread (z-axis) or the optical axis of the camera. After a 360° rotation, the reference surface returns to the same angle relative to the camera but at a different position in height (different z-position). In addition, it is advantageous to generate images at the intermediate positions of 90°, 180° and 270°. Given the angled position of the reference surface and the rotation about the optical axis, the target alternately assumes positive and negative angular positions about the x- and y-axes of the camera.

This allows the angle of the reference surface relative to the camera to change during rotation within a wide angular range so that a plurality of intermediate positions can be measured.

Advantageously, the flat reference surface can have a plurality of square markings which are arranged at known distances relative to each other.

Using the markings, the precise position of the reference surface relative to the camera can hence be determined. Known calibration methods can be used for this.

BRIEF DESCRIPTION OF THE DRAWINGS

The invention will be explained with reference to the drawings. In the figures.

EXEMPLARY EMBODIMENT

Figure 1:
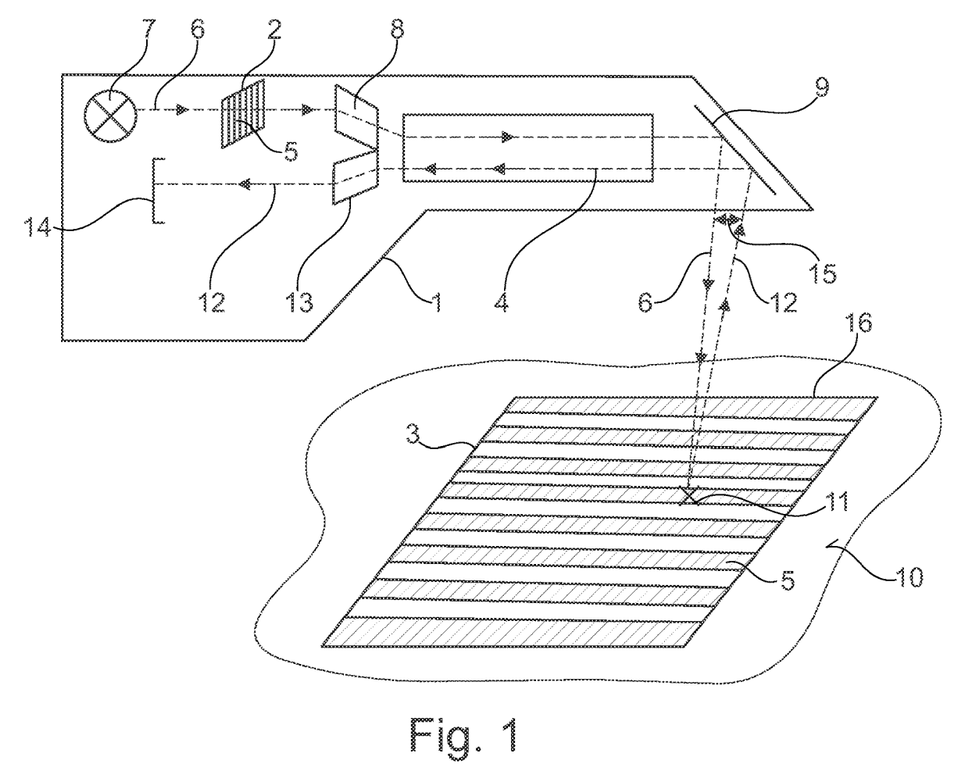
FIG. 1 shows a sketch of a dental camera which is based on the fringe projection method.

FIG. 1 shows a sketch of a dental camera 1 which involves a fringe projection method for three-dimensional optical measurement. The dental camera 1 comprises a projection grid 2 for generating a projection pattern 3 that consists of a plurality of parallel fringes, and an optical system 4 that projects the generated projection pattern 3 onto the object to be measured (not shown). The projection grid can for example be a slide with a plurality of parallel fringes 5. An illuminating beam 6 is generated by a light source 7 such as an LED and passes through the projection grid 2, is deflected by means of a deflection prism 8, and is then projected by means of the optical system 4 and a deflection mirror 9 onto the object 10 to be measured. The object 10 can for example be the surface of a tooth. The illuminating beam 6 is reflected as an observation beam 12 by a measurement point 11 which is shown as a cross. The observation beam 12 is then deflected by the deflection mirror 9, by the optical system 4, and by a second deflection prism 13 to an image detector 14. The image detector 14 can for example be a CCD detector or a CMOS detector. By using a fringe projection method, a 3-D coordinate of the measurement point 11 is determined relative to the dental camera 1 using a triangulation angle 15 between the illuminating beam 6 and observation beam 12, and using the known positions of the light source 7 and the image detector 14. In this manner, the object to be measured 10 is completely measured within a measuring field 16 of the projected projection pattern 3. To identify the individual fringes 5 of the projection pattern 3, the individual fringes can be encoded using different light properties such as intensity, color, polarization, coherence, phase, contrast, location or propagation time.

With a color coding, a given fringe can be uniquely identified with reference to the neighboring fringes, wherein for example a sequence of four neighboring colored fringes or three color transitions can be uniquely coded.

With a coding using the phase, the individual fringes may have a sine pattern longitudinal to the path of the fringes 5, wherein the phase of the sine pattern for the individual fringes 5 is slightly shifted. The respective fringes can be uniquely identified using the phase shift.

The fringe width of such fringe projection methods can for example be 150 μm in the measuring field 16 of the object to be measured 10.

Production errors of the projection grid 2 and imaging errors of the optical system 4 can cause the projection pattern 3 to be imaged in a distorted manner. This leads to measuring errors when determining the 3-D coordinates of the measurement points on the surface of the measured object 10. To compensate for these measuring errors, the present inventive method is executed.

Figure 2:
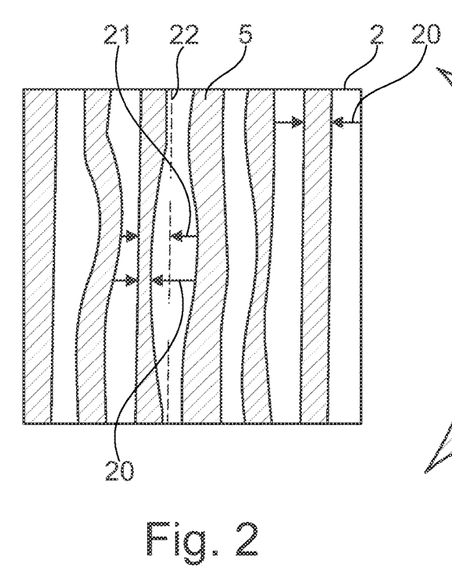
FIG. 2 shows a sketch of a distorted projection grid from FIG. 1.

FIG. 2 shows a sketch of the projection grid 2 according to FIG. 1 with parallel fringes 5 which vary in brightness. The dark fringes are depicted with parallel line shading. The fringes 5 are distorted by production errors such that an actual fringe width 20 of the individual fringes 5 differs from a target fringe width (desired fringe width) 21. For example, a target fringe edge 22 is depicted with a dashed line at the third fringe from the left. This deviation between the actual fringe width 20 and the target fringe width 21 leads to measuring errors in the generated three-dimensional image.

Figure 3:
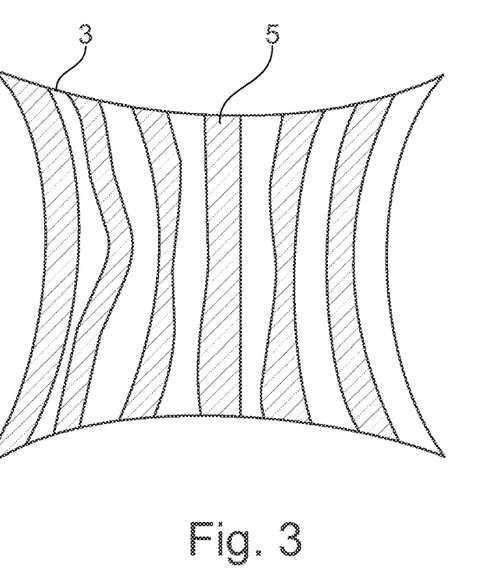
FIG. 3 shows a sketch of a distorted projection pattern.

FIG. 3 shows the projection pattern 3 with fringes 5 projected onto the object 10 according to FIG. 1, wherein the fringes according to FIG. 2 distorted by production errors are additionally distorted by the imaging errors of the optical system 4 according to FIG. 1. The so-called optical distortions can be in any form. In the present case, the distortion is pillow-shaped, with the corners of the projection pattern 3 being pulled apart. The distortion could also be a rotationally symmetrical barrel-shaped distortion, wherein the corners of the projection pattern are distorted toward the middle. These optical distortions hence also lead to a measuring error of the three-dimensional image of the object 10.

Figure 4:
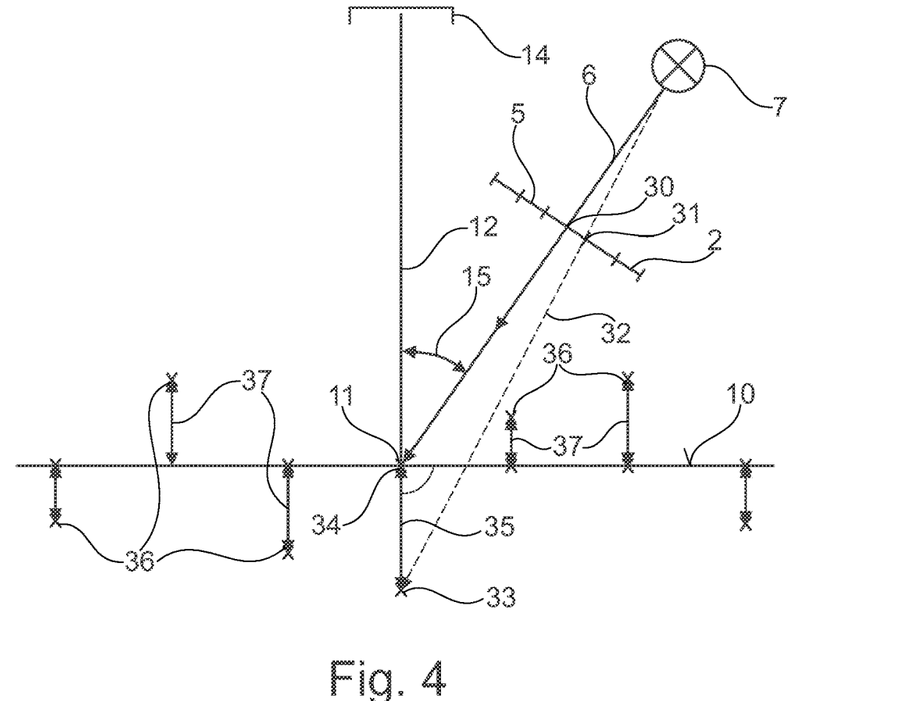
FIG. 4 shows a sketch of a camera model of the dental camera from FIG. 1.

FIG. 4 shows a sketch to illustrate the present method, wherein a camera model of the dental camera according to FIG. 1 is shown. The light source 7 emits the illuminating beam 6. The projection grid 2 has a plurality of parallel fringes 5 which are indicated by short dashes. The projection pattern is projected onto the surface of the measuring object 10. In a schematic illustration, the illuminating beam 6 is reflected at a measurement point 11, and is reflected as an observation beam 12 back to the image detector 14. The 3-D coordinates of the measurement point 11 relative to the dental camera 1 are then calculated using the triangulation angle 15 and the positions of the light source 7 and image detector 14. Due to the distortions of the projection pattern 3 caused according to FIGS. 2 and 3, a desired target fringe edge 30 is shifted relative to the actual erroneous fringe edge 31. In the process, the illuminating beam 6 is also shifted to an altered illuminating beam 32 (dashed line). The shifted erroneous illuminating beam 32 intersects the observation beam 12 at an actual coordinate 33 of the measurement point 11. This actual coordinate 33 deviates significantly from a target coordinate 34 of the measurement point 11. To perform the calibration, the object to be recorded 10 is a flat reference surface. For calibration, a deviation 35 is determined between the actual coordinate 33 and target coordinate 34 of the measurement point 11. The deviation 35 can for example be determined perpendicularly to the reference plane 10. In this manner, the actual coordinates 36 and deviations 37 from the other measurement points on the reference plane 10 are determined. To determine the precise position of the reference plane 10 relative to the dental camera 1, the reference plane can have markings with known distances from each other. Using the markings, the precise position of the reference plane 10 can be determined relative to the dental camera 1 and then relative to the deviations 35, 37.

Alternately, a reference plane can be fitted by the determined actual coordinates 33, 36, and the deviations between the actual coordinates 33, 36 and the reference plane can then be determined. Based on the deviations 35, 37, compensation values are then determined for the individual fringes 5 which compensate for these deviations.

Figure 5:
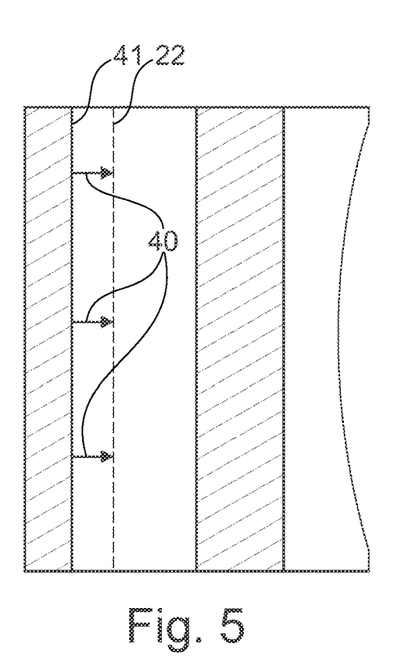
FIG. 5 shows a sketch to illustrate a compensation method step.

FIG. 5 shows a sketch to illustrate the compensation step of the method. Starting with the deviations 35, 37, a compensation value 40 is calculated that indicates a necessary shift of an actual fringe edge 41 relative to the desired target fringe edge 22 in order to compensate for the deviations 35, 37 of the actual fringe edge 41. In this manner, compensation is carried out for all of the other fringes 5 according to FIG. 3.

Figure 6:
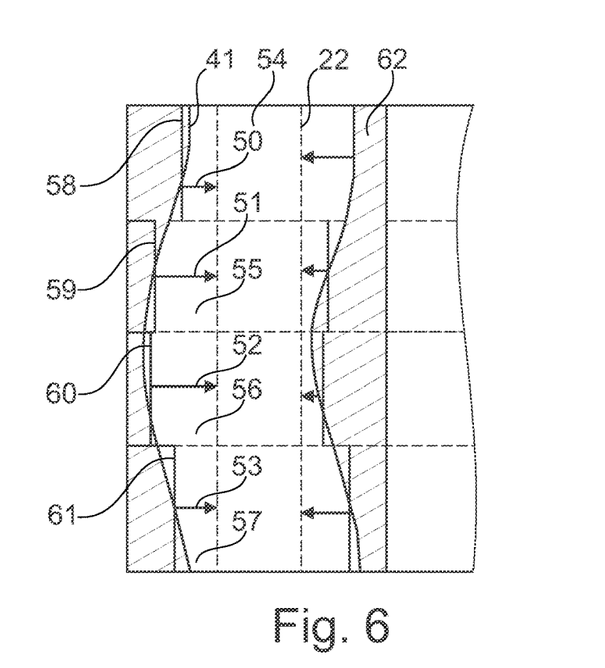
FIG. 6 shows a sketch to illustrate another embodiment of the compensation method step.

FIG. 6 shows a sketch of a second embodiment of the compensation step of the method. In comparison to FIG. 5, for the actual fringe edge 41, not just one compensation value but rather a plurality of compensation values 50, 51, 52 and 53 are determined for four sectors 54, 55, 56 and 57. The average values 58, 59, 60 and 61 for the individual sectors 54, 55, 56 and 57 of the actual fringe edge are determined, and then the deviations 50, 51, 52 and 53 from the target fringe 22 are determined. In this manner, the compensation values are determined for the different sectors 54, 55, 56 and 57 as well as for the other fringes 5 as illustrated with reference to a second actual fringe edge 62. A matrix of compensation values is hence calculated which is used on the projection pattern 3 in a compensation method step while measuring the object 10 to correct the projection pattern 3. Then using the corrected projection pattern, the three-dimensional image of the object 10 is calculated.

Figure 7:
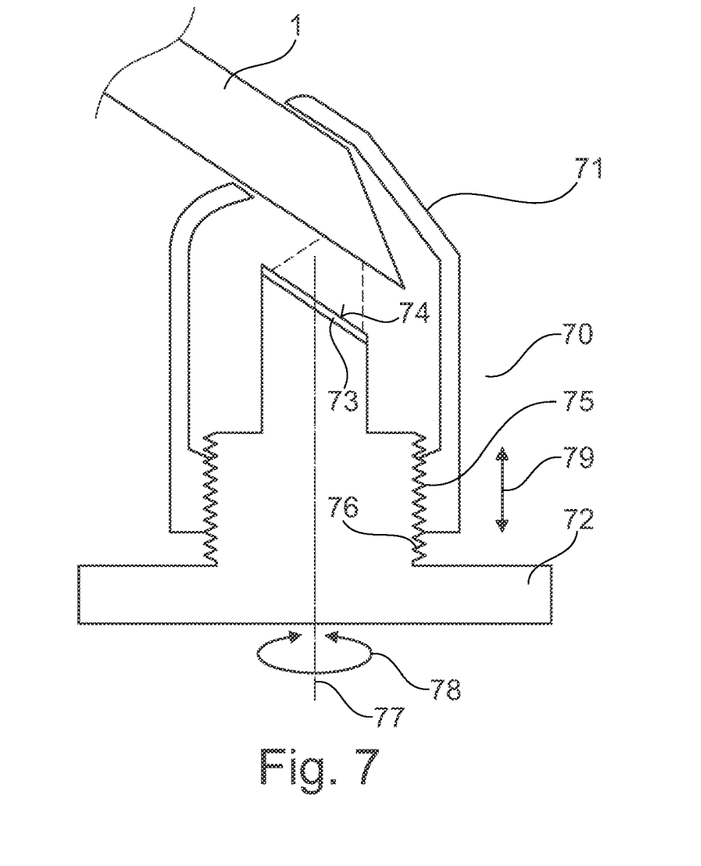
FIG. 7 shows a sketch of a calibration device.

FIG. 7 shows a sketch of a calibration device 70 which has a first holding device 71 for the dental camera 1 according to FIG. 1, and a second holding device 72 for a calibration plate 73 with a reference surface 74. The first holding device 71 has an inner thread 75, and the second holding device 72 has an outer thread 76, and these two threads engage. By rotating the second holding device 72 relative to the first holding device 71 around an axis of rotation 77 as shown by the arrow 78, the position and orientation between the dental camera 1 and reference surface 74 are thereby changed in a defined manner as indicated by the arrow 79. The inner thread 75 and outer thread 76 can have snap-in devices to ensure rotation 78 in defined steps. This allows a plurality of images of the reference surface 74 to be repeatedly taken at specific intervals and with defined angles between the dental camera 1 and the reference surface 74. The calibration method can hence be performed for different distances and angles such that a matrix consisting of compensation values 50, 51, 52 and 53 according to FIG. 6 is determined. Depth-dependent measuring errors caused by optical distortions can be compensated in this manner.

Figure 8:
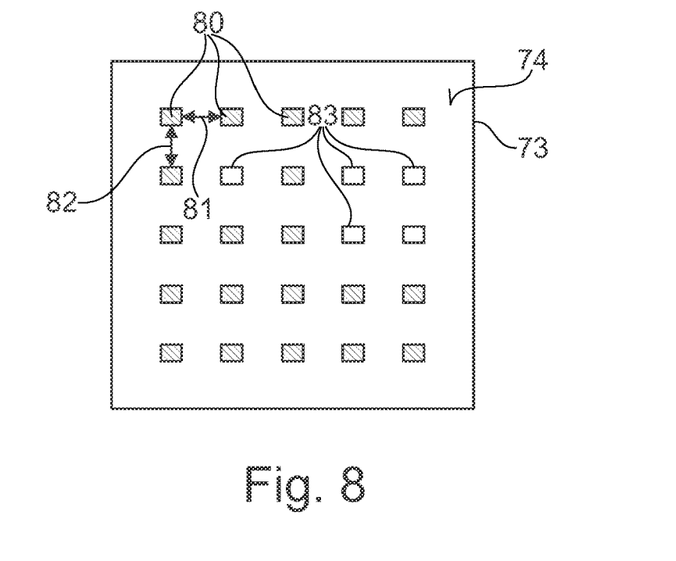
FIG. 8 shows a calibration plate with markings.

FIG. 8 shows the calibration plate 73 with the reference surface 74 according to FIG. 7, wherein the reference surface 74 is provided with markings 80 which are at specific distances 81, 82 relative to each other. The markings can also be of differing brightnesses. By means of a characteristic pattern 83 consisting of bright markings, the precise position of the respective image on the reference surface 74 can be determined. The adjusted position and alignment of the reference surface relative to the dental camera 1 can hence be checked.

REFERENCE NUMERALS 1 dental camera
2 projection grid
3 projection pattern
4 optical system
5 parallel fringes
6 illuminating beam
7 light source
8 deflection prism
9 deflection mirror
10 measured object
11 measurement point
12 observation beam
13 deflection prism
14 image detector
15 triangulation angle
16 measuring field
20 actual fringe width
21 target fringe width (desired fringe width)
30 target fringe edge (desired fringe edge)
31 actual fringe edge
32 illuminating beam
33 actual coordinate
34 target coordinate (desired coordinate)
35 deviation
36 actual coordinates
37 deviations
40 compensation value
41 actual fringe edge
50 compensation value
51 compensation value
52 compensation value
53 compensation value
54 first sector
55 second sector
56 third sector
57 fourth sector
58 first average value
59 second average value
60 third average value
61 fourth average value
70 calibration device
71 first holding device
72 second holding device
73 calibration plate
74 reference surface
75 inner thread
76 outer thread
77 axis of rotation
78 rotational movement
79 adjustment
80 markings
81 first distance
82 second distance
83 pattern of bright markings.

The invention claimed is:
1. A method for calibrating a dental camera, based on a fringe projection method; comprising;
generating a projecting pattern that includes a plurality of fringes using a projection grid,
coding each fringe of the plurality of fringes such that each fringe of the plurality of fringes is uniquely identified and individually and automatically controlled and displaced in a displacing step;

projecting the generated projection pattern onto a dental object to be measured using an optical system, the method further comprising;

measuring a reference surface of a calibration plate having a plurality of predetermined markings, said measuring including using the plurality of fringes to determine actual coordinates of a plurality of measurement points, comparing the determined actual coordinates with predetermined target coordinates of the plurality of measurement points, determining deviations between the actual coordinates and the predetermined target coordinates, and calculating a plurality of compensation values for individual fringes of the projection pattern, compensating for the deviations between the actual coordinates and the target coordinates during measurement of the dental object by:

correcting said projection pattern by:
individually and automatically displacing, in said displacing step, an edge of one or more of the uniquely identified fringes of the projection pattern in a plane of the projection grid from an actual fringe edge to a target fringe edge using said calculated plurality of compensation values, wherein the plurality of predetermined markings are used to determine the precise position and alignment of the calibration plate relative to the dental camera and, wherein deviations between the actual coordinates and the calibration plate are determined along a direction perpendicular to the calibration plate.

2. The method according to claim 1, characterized in that the reference surface is a plane, and the deviations between the actual coordinates and the predetermined target coordinates are determined by fitting a reference plane using the actual coordinates by means of the least squares method, and then the deviations between the actual coordinates and the reference plane are determined along a direction perpendicular to the reference plane.

3. The method according to claim 1, characterized in that the deviations between the actual coordinates and the predetermined target coordinates are determined from a plurality of images for different distances and alignments of the reference surface relative to the dental camera.

4. The method according to claim 3, characterized in that the images are taken using a calibration device which has a first holding device for the dental camera and a second holding device for the reference surface which are displaced in a specific manner in several steps relative to the first holding device.

5. The method according to claim 1, further comprising:
calculating only one compensation value for each edge of a fringe to indicate a necessary displacement of this edge in said plane of the projection grid.

6. The method according to claim 1, further comprising:
dividing each edge of a fringe into a plurality of sectors, calculating a compensation value for each sector, and individually and automatically displacing each sector in the plane of the projection grid according to the corresponding calculated compensation value of the sector to compensate for the deviations for this sector.

7. The method according to claim 1, characterized in that the deviations between the actual coordinates and predetermined target coordinates are determined by taking a plurality of three-dimensional images of the reference surface in the same position and alignment relative to the dental camera, wherein the deviations from the individual images are averaged in order to reduce non-systematic errors generated by a noise signal.

8. The method according to claim 1, wherein the coding step involves color coding wherein each fringe is colored or a phase coding wherein a phase of a sine pattern for each fringe is shifted.

9. A calibration apparatus for calibrating a dental camera comprising;
a projection grid constructed to generate a projection pattern that includes a plurality of fringes,
an optical system constructed to project the generated projection pattern onto a dental object to be measured,
a first holding device for holding the dental camera,
a reference surface including a plurality of predetermined markings constructed for alignment, and
a second holding device for holding the reference surface,
wherein the first holding device is configured to be displaced relative to the second holding device such that a number of defined distances and/or alignments are adjusted between dental camera and the reference surface, wherein the first holding device has an inner thread, and the second holding device has an outer thread which engages in the inner thread of the first holding device, wherein by rotating the first holding device relative to the second holding device, the distance and alignment of the dental camera relative to the reference surface is changed in defined steps wherein the reference surface is disposed on the second holding device at an angle of between 50° and 70° relative to a middle axis of the outer thread of the second holding device.

10. The calibration device according to claim 9, wherein the reference surface has a plurality of square markings which are arranged at known distances relative to each other.

11. A method for calibrating a dental camera based on a fringe projection method for the three-dimensional optical measurement of an object, comprising;
measuring a reference surface having known dimensions using the fringe projection method,
determining actual coordinates of a plurality of measurement points on the reference surface;
comparing the determined actual coordinates with predetermined target coordinates of the plurality of measurement points; and,
calculating a plurality of compensation values for the individual fringes of the projection pattern based on deviations between the actual coordinates and the target coordinates;
wherein during the measurement of the object the calculated compensation values are taken into account in order to compensate for the deviations between the actual coordinates and the target coordinates;
wherein the calibration is carried out using a calibration device having a first holding device for the dental camera and a second holding device for the reference surface; wherein the first holding device is adjusted relative to the second holding device such that several defined distances and/or alignments between the dental camera and the reference surface are set; wherein the distance and the alignment of the dental camera relative to the reference surface is changed in defined steps via the rotation of the first holding device relative to the second holding device by using of a thread; wherein the reference surface is arranged on the second holding device at an angle of between 50° and 70° relative to a center axis of the outer thread of the second holding device.

\* \* \* \* \*